United States Patent [19]
Hepburn et al.

[11] Patent Number: 5,014,690
[45] Date of Patent: May 14, 1991

[54] ADJUSTABLE SPLINT

[76] Inventors: George R. Hepburn, 443 Gainsborough Ct., Severna Park, Md. 21146; Dror Paley, 2001 W. Rogers Ave., Baltimore, Md. 21209

[21] Appl. No.: 483,124

[22] Filed: Feb. 22, 1990

[51] Int. Cl.[5] .......................... A61F 3/00; A61F 5/00
[52] U.S. Cl. ............................... 128/80 H; 128/80 R; 128/88; 128/166; 128/581
[58] Field of Search .................. 128/80 R, 80 H, 581, 128/88, 87 R, 166; 36/35 A, 31, 81; 606/56

[56] References Cited

U.S. PATENT DOCUMENTS

| | | | |
|---|---|---|---|
| 2,477,591 | 8/1949 | Follis | 128/80 H |
| 2,516,872 | 8/1950 | Hauser et al. | 128/80 H |
| 3,064,644 | 11/1962 | Patterson | 128/80 H |
| 4,485,808 | 12/1984 | Hepburn | 128/87 R |
| 4,657,000 | 4/1987 | Hepburn | 128/88 |
| 4,771,768 | 9/1988 | Crispin | 128/80 H X |
| 4,834,078 | 5/1989 | Biedermann | 128/80 R X |
| 4,934,355 | 6/1990 | Porcelli | 128/80 H |

Primary Examiner—Richard J. Apley
Assistant Examiner—Jennifer L. Doyle
Attorney, Agent, or Firm—Larson & Taylor

[57] ABSTRACT

An adjustable spring-loaded splint device is provided for supporting the ankle joint of a wearer. The splint device includes a pair of spaced lower struts and a pair of spaced upper struts pivotally connected to lower struts. The lower struts each include, at one end, a pivotably mounted head portion defining a cam surface, and the upper struts each include an adjustable spring assembly mounted therein, including a spring biased into engagement with the cam surface, for applying a quantifiable force tending to align the upper and lower struts. Upper and lower sets of cuff and strap members are connected between the upper struts which adjustably and releasably secure the splint device to the limb of the wearer using a detachable fastener including hooks and loops fastener sections. An adjustable footplate assembly is pivotally connected to the lower struts of the splint device for securely supporting the foot of the wearer in a selected relation with respect to the ankle. An elevating sole, which is of variable thickness and is adapted to be secured to footplate assembly, can be used in supporting the foot at a given height above the ground.

17 Claims, 6 Drawing Sheets

ADJUSTABLE SPLINT

BACKGROUND OF THE INVENTION

1. Field of the Invention

This invention relates to an adjustable splint, and more particularly, to an adjustable splint useful in treating impairments in the ankle joint, from flexion or extension contracture, weakness in the supporting musculature, or other maladies inhibiting the integrity of the body joint in accomplishing extension or flexion.

2. Prior Art

There are numerous cases where bedridden individuals have lost ambulation simply from developing an ankle flexion contracture. The various causes of developing ankle flexion contractures in this segment of the population are many. Very frequently, disuse and neglect of an existing medical problem such as a stroke, fracture about the ankle or vascular problems, just to mention a few, will result in the development of an ankle flexion contracture. In addition, people having any type of ankle surgery, especially medial meniscectomies, open reduction and internal fixation of a fracture and ligamentous repairs, are subject to developing an ankle flexion contracture. There are also other injuries about the ankle not requiring surgery which develop into ankle flexion contracture. These injuries include minuscule tears, ligament tears (both partial and complete) and fractures about the ankle which are reduced by close reduction. If these ankle flexion contractures, whatever their cause, could be reduced, more than 50 percent of all bedridden patients having ankle flexion contractures would gain tremendous progress toward gaining independence in ambulation.

People also develop extension contractures in the ankle joint for many and various causes. Weakness, disuse, fractures, surgeries, traumatic injuries, illness and other causes have been known to cause loss of ability to flex the ankle, i.e., to produce extension contracture of the ankle.

Devices for reducing extension contractures by providing adjustable, qualifiable pressure to various parts of the body have been previously disclosed by the inventor in, for example, U.S. Pat. Nos. 4,657,000 and 4,485,808. However, no device presently exists which is specifically concerned with reducing extension contractures about the ankle joint by providing adjustable, qualifiable pressure.

Splint devices and mechanisms have been designed to be influential at the ankle either for support or mobilizing the ankle joint. However, these devices are either not designed to reduce ankle flexion or extension contracture, or when designed for a similar purpose, cannot be tolerated by the patient population for a long enough period to effectively reduce a contracture. Moreover, none of these prior art devices offer a satisfactory means for adjusting the pressure exerted by the splint devices.

OBJECTS OF THE INVENTION

Accordingly, it is a object of the invention to provide an improved splint device for reducing flexion or extension contractures about an ankle joint.

Another object of the invention is to provide a splint device which will shorten the rehabilitation time of individuals that are bedridden or incapacitated due to flexion or extension contractures about an ankle joint.

Yet another object of the invention is to provide a splint device which allows easy gradual adjustment to the quantifiable force desired on an extremity acting across an ankle joint.

A further object of the invention is to provide a splint device for incapacitated patients having a disability about the ankle joint to help obtain a higher level of independence in their activities of daily living, self-care and ambulatory activities.

A further object is to provide an improved splint for providing support to an ankle joint in cases where muscular weakness exists.

SUMMARY OF THE INVENTION

In accordance with a preferred embodiment of the invention, an adjustable splint device is provided for supporting the ankle of a wearer, which splint device comprises: (a) a pair of strut assemblies adapted to be positioned on opposite sides of the ankle of a patient or other wearer, each of the strut assemblies comprising an upper strut, and a lower strut pivotably connected to said upper strut, at least one of the struts including, at one end thereof, a pivotably mounted head portion defining a cam surface, and the upper strut including an adjustable biasing means, mounted therein and biased into engagement with said cam surface, for applying a quantifiable force tending to align or approximate said upper and lower struts; (b) foot support means, connected to the pair of strut assemblies, for supporting the foot of the wearer; the foot support means comprising a foot support device; pivot means for pivotably connecting said foot support device to the lower struts of said strut assemblies; and adjustable locking means for selectively fixing the angular position of the foot support device relative to said lower struts so that the foot of the wearer is held in a predetermined position relative to the ankle of the wearer; and (c) securing means for releasably securing the strut assemblies to the lower leg of the wearer.

In one preferred embodiment, the foot support device comprises a pair of laterally adjustable footplates. In this embodiment, each footplate advantageously includes an upwardly projecting portion at the outermost edge thereof having an arcuate slot therein, the aforementioned pivot means comprises a connection plate disposed at the distal end of, and pivotably connected to, a respective projecting portion, and the aforementioned locking means comprises an adjustable fastening means extending through the arcuate slot for fixing the position of the connection plate relative to said projecting portion.

Preferably, the splint device includes, in this embodiment, width setting means for adjustably setting the lateral positions of the foot support plates so as to accommodate different foot widths. In a preferred implementation, the width adjustment means includes at least one adjustment screw located on an underside area of the foot support plates for engaging said foot support plates to thereby set a predetermined width.

In accordance with a further aspect of the invention, the splint device further comprises adjustable length setting means for adjustably setting the axial position of foot support means relative to the remainder of the splint device so as to selectively shorten or lengthen the splint device. Preferably, each lower strut includes a pair of telescoping sections and the said length adjusting means includes at least one set screw for fixing the relative positions of said telescoping sections so as to set the combined length of the sections.

In an advantageous embodiment, the securing means comprises adjustable instep strap means, connected to at least one pair of the struts, for engaging the front of the ankle joint of the wearer. Preferably, the instep strap means comprises a resilient tube and a fastening means, which includes at least one hooks and loops fastener and which is of adjustable length and extends through said tube, for fastening said tube to said splint assemblies.

Additionally or alternatively, the securing means comprises strap means, attached to and extending between at least one pair of struts of each said strut assembly, for securing the splint assemblies to the limb of a wearer above the ankle joint. In a preferred embodiment, the strap means comprises: (a) a first lower strap of a length sufficient to wrap across the shin area of the limb of a wearer and means for adjustably and releasably fastening said first strap between the strut assemblies; (b) a second lower strap of a length sufficient to wrap across a lower rear area of the limb of a wearer and means for adjustably and releasably fastening said second strap between the strut assemblies; (c) a first upper cuff of a length sufficient to wrap across an upper shin area of the wearer and means for adjustably and releasably securing said first cuff between the strut assemblies; and (d) a second upper cuff having a length sufficient to wrap across a calf area of the wearer and means for adjustably and releasably securing said second cuff between the strut assemblies. Advantageously, the first and second upper cuffs are of the same width, and the first and second lower straps are of the same width and are more narrow in width than the upper cuffs. Preferably, the first and second upper cuffs each comprise, at least one end thereof, fastening means comprising a loops fastener section spaced apart from a hooks fastener section.

In accordance with a further embodiment of the overall invention, the foot support device includes a shoe device in which the foot of the wearer can be received. Preferably, the shoe device includes a sole of variable height. The sole advantageously comprises a plurality of stacked, removably mounted sole members which can be removed to change the height of the sole. In this embodiment, the shoe device includes a sole having an upper slot therein and the foot support device further includes a pair of laterally adjustably overlapping plates which are received in said slot and which connect said shoe to said strut assembly.

Other features and advantages of the invention will be set forth in, or apparent from, the following detailed description of preferred embodiments of the invention.

BRIEF DESCRIPTION OF THE DRAWINGS

The nature of the invention will appear more clearly from the following detailed description when taken in connection with the following drawings which show, by way of example, preferred embodiments of the invention.

In the drawings.

DESCRIPTION OF THE PREFERRED EMBODIMENTS

Figure 1:
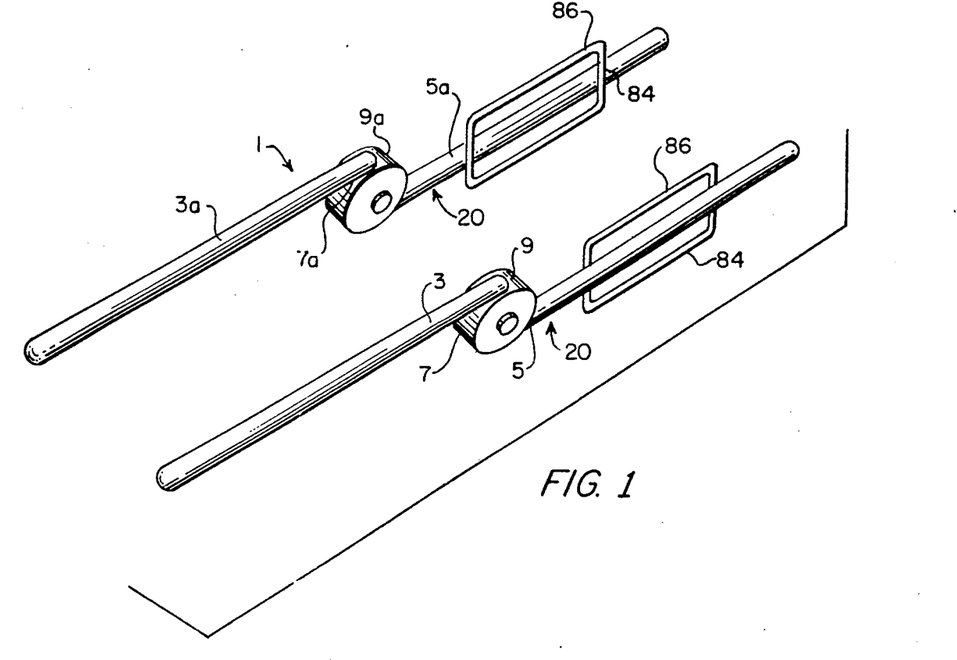
FIG. 1 is a perspective view of a pair of strut assemblies of an adjustable splint according to the invention.

Referring to FIG. 1, an adjustable splint device 1 is shown comprised of lower struts 3 and 3a and upper struts 5 and 5a. Lower struts 3, 3a contain rounded head portions 7, 7a, and upper struts 5, 5a contain socket head portions 9, 9a, which receive head portions 7, 7a, respectively, for pivotable engagement therewith.

Figure 2:
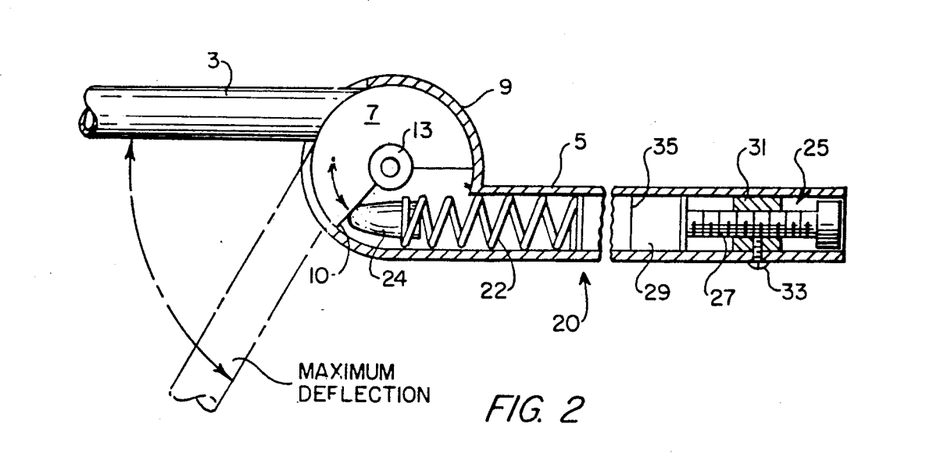
FIG. 2 is a side elevational view of one of the strut assemblies of FIG. 1 showing the adjustable spring-loaded tension control mechanism mounted therein.
Figure 3:
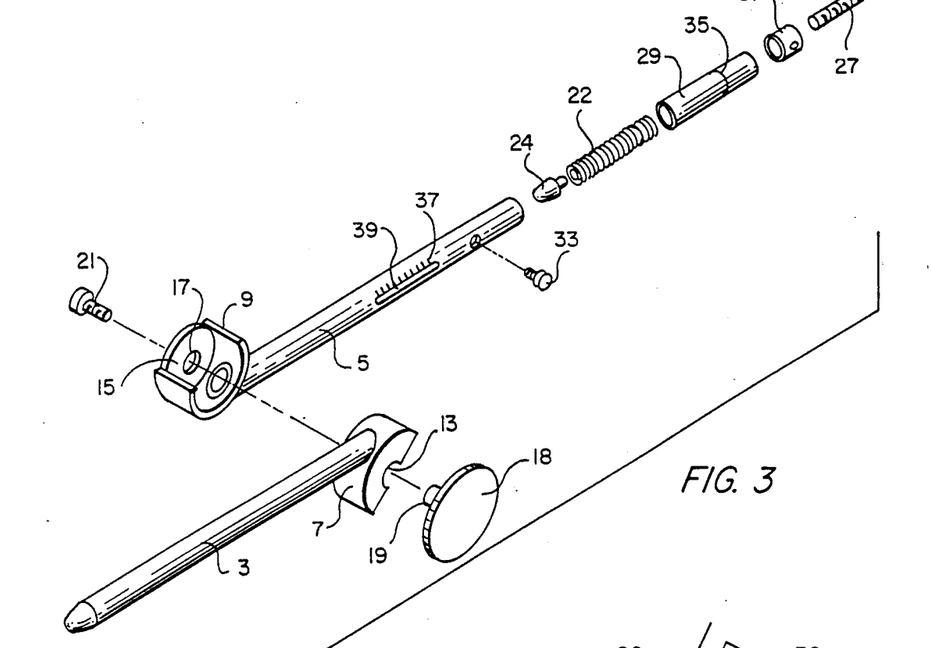
FIG. 3 is an exploded perspective view of one of the strut assemblies of FIG. 1.

In FIGS. 2 and 3, rounded head portion 7 is shown cut away and, as shown, defines a cam surface 10 and is provided with a axial surface recess 13. A similar structural arrangement exists also in rounded head portion 7a, although for simplicity, a detailed description is given only with respect to head portion 7. A first surface plate 15 having a screw hole 17 covers one side of the combined head portion 7-9 and a second plate member 18 having a threaded protruding member 19 covers the other half of the combined head portions 7-9. When surface plate number 18 is positioned over the combined head portion 7-9, protruding member 19 projects through the axial circular recess 13 and receives a screw 21 through screw hole 17. Lower strut 3a and upper strut 5a are similarly pivotably connected by corresponding members bearing like numbers but carrying the designating suffix "a".

The lower and upper struts may be constructed of any material of sufficient strength such as plastic, metal, wood and the like. Particularly preferred are struts made of stainless steel metal. At least one of the struts should be at least partially hollow so as to house therein the adjustable spring mechanism of the invention. Most advantageously, all of the struts are tubular in construction so as to provide a lightweight product and if desired each of the struts 3, 3a, 5 and 5a can be comprised of two telescoping portions, as shown for example in FIG. 5, by portions 3, 3' and 3a, 3a', so as to permit lengthening or shortening of the struts. Such a telescoping feature provides a splint which can be adjusted, by means of an adjustment screw 6, 6a, to several different lengths allowing the splint to fit a greater number of individuals.

An adjustable spring-loaded tension control mechanism is generally designated 20 (FIG. 2). Although such a mechanism can, in theory, be provided in either the lower or the upper struts, in the preferred embodiment illustrated, the upper struts 5 and 5a each include a respective adjustable spring mechanism 20. Each adjustable spring mechanism 20 is comprised of a spring 22 to which is attached a nose element 24 that bears on cam surface 10. Coil or clock springs are generally preferred but in some instances leaf springs may be employed. An adjustable screw device indicated generally as 25 abuts the other end of the spring 22 and produces a quantifiable force which tends to approximate, i.e., bring together, the lower strut 3 with the upper strut 5 and the lower strut 3a with upper strut 5a. As maximum flexion is approached, tension is created in the compression coiled spring 22. The adjustable screw device 25 is comprised of a head screw 27, which could be, for example either a slotted head screw or an "Allen" head screw, threaded to a spring-abutting member 29. The head screw 27 is fixed within upper strut 5 by screw 33. Head screw 27 receives, and is turned by, a screw adjust tool 32 (shown in FIG. 4 discussed below), such as a conventional (slotted head) screwdriver or an "Allen" socket wrench. The turning of the screw creates greater compression of spring 22, thereby exerting greater force on the cam surface 10 of the lower strut 3 to exert a one way tension. The tension capability of the spring mechanism 20 can cover almost any practical range, with a range of from 0 pounds tension to 10 pounds of tension being typical. Also, the tension exerted by the spring 22 can be varied at any point of joint range of motion, say from 60° flexion to 0° flexion of the ankle joint. The spring mechanism can be calibrated to exert this range of tension by providing spring-abutting member 29 with a poundage indicator line 35 and a calibration scale 37 (FIG. 3). Scale 37 has a slot 39 through which the poundage indicator 35 (FIG. 2) is visible.

While in the preferred embodiment of the invention, the adjustable tensioning or biasing mechanism comprises a spring device other devices such as an hydraulic powered biasing unit can be used.

As mentioned above and described in more detail below, the splint device of the present invention involves the addition to the basic overall adjustable strut assembly (or pair of strut assemblies) of FIGS. 1 to 3 of an adjustable footplate unit or assembly together with an arrangement for securing the strut assembly, and footplate assembly to the limb and ankle in the area of the ankle joint. Referring to FIGS. 4 to 7, the overall strut assembly comprising upper strut 5 and 5a, lower struts 3 and 3a and socket head portions 9, 9a, and associated biasing mechanisms 20, as described above in connection with FIGS. 1 to 3, is combined with a footplate assembly generally denoted 40, an upper cuff assembly 42 and a lower strap assembly 44, all of which are described in more detail below.

Figure 4:
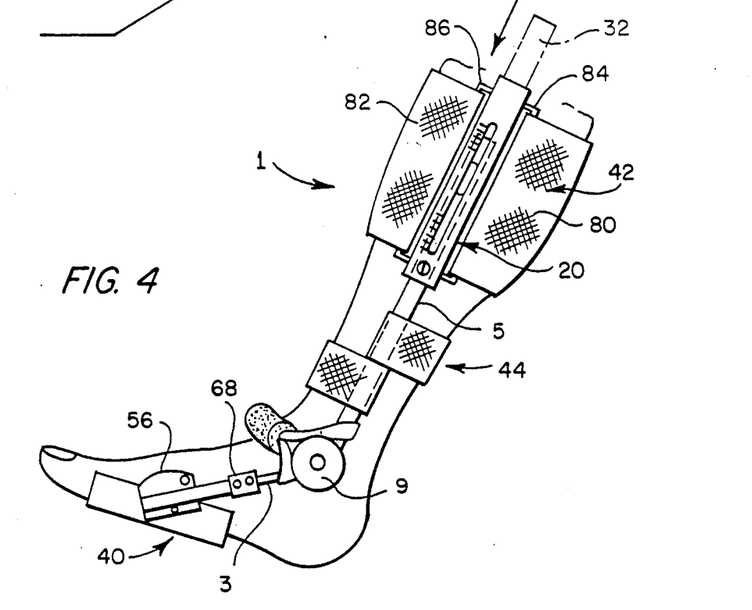
FIG. 4 is a side elevational view of an adjustable splint device according to the invention shown in place on a patient.
Figure 5:
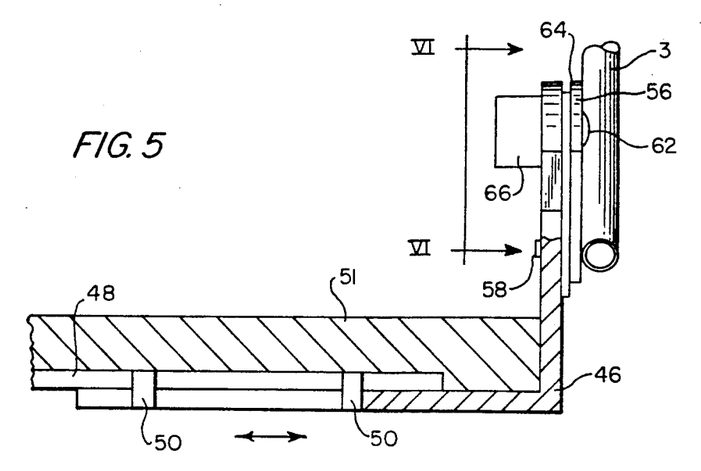
FIG. 5 is an end elevational view, partially broken away, of the footplate assembly of FIG. 4.
Figure 6:
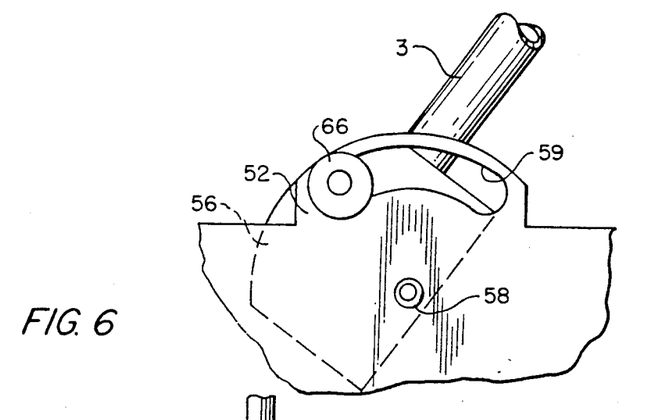
FIG. 6 is a side elevational view, partially broken away, of the footplate assembly of FIG. 4.
Figure 7:
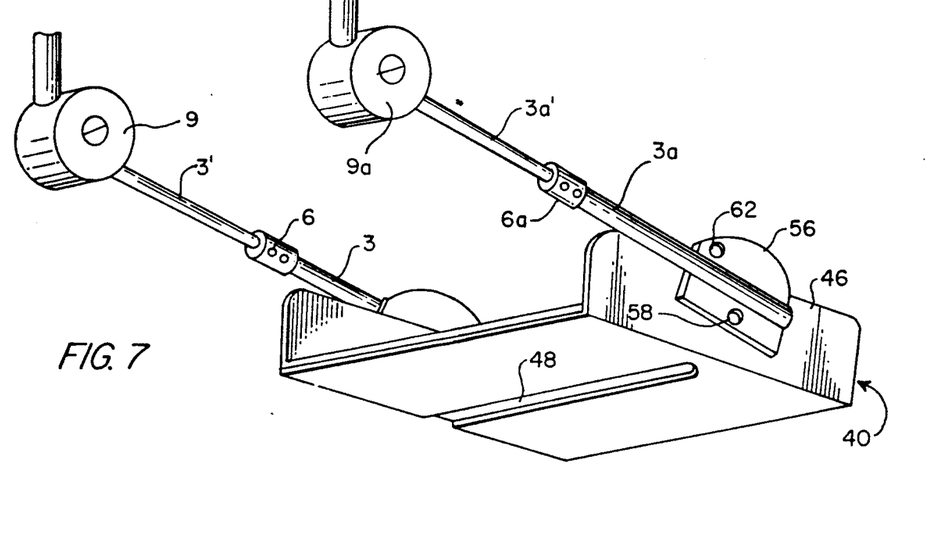
FIG. 7 is a bottom perspective view of the splint device of FIG. 4.

The footplate assembly 40 is perhaps best seen in FIGS. 5 to 7 and, as shown, comprises a pair of L-shaped foot plates 46 and 48 (FIGS. 5 and 7) which receive the foot of a patient (FIG. 4). As indicated by the double headed arrow in FIG. 5 the overlapping base portions of footplates 46, 48 can be moved relative to move another to vary the width of the foot receiving area defined by footplates 46, 48 and to thus accommodate feet of different widths. As shown in FIG. 5, set screws 50, which extend through the two base portions of footplates 46, 48 can be used to fix the relative positions of the two footplates 46 and 48. For example, the plates may include a plurality of laterally spaced screw holes disposed (not shown) across the widths thereof and arranged in a row perpendicular to the longitudinal axis of the plates, which holes can be brought into registry to enable the plates to be fixed in place by screws 50. Alternatively, aligned slots (not shown) can be used which form a tight fit with screws 50 so that footplates 46, 48 are held in place with the desired lateral separation. A shaped foot pad 51 (FIG. 5) is fitted o the upper surfaces of footplates 46, 48 to provide added comfort.

It will be appreciated that the mounting arrangements for connecting the corresponding struts 3, 3a of the strut assembly to footplates 46 and 48 are basically the same, and thus considering footplate 46 as exemplary, and referring particularly to FIGS. 5 and 6, plate 46 includes an upstanding portion 52 at the upper edge thereof in which is formed an arcuate slot 54. Corresponding lower strut 3 has welded or other affixed to the distal end thereof a plate 56 of a shape somewhat similar to that of upstanding portion 52. The base portion of plate 52 is pivotally connected to the side of footplate 46 by a pivot shaft 58 and a spacer 60, while the combination of a screw 62, a spacer 64 and a shaped nut 66 is secured to plate 46 such that nut 66 is received in and extends beyond arcuate slot 54 so as to limit the pivoting movement of plate 56 and to enable plate 56, and thus strut 3, to be fixed in position relative to footplate 46 by simply tightening screw 62.

As noted above, plates 46 and 48 can be shifted laterally with respect to one another to vary the width of footplate assembly 40 further, the length of lower struts 3 and 3a can be varied by suitable means such as set screws 68. For example, "Allen" screws and slotted head screws, corresponding to screws 68, can be provided which, in use, are released or removed so as to permit the two telescoping sections making up the struts 3 and 3a to be pulled apart or telescoped together until the strut is of the desired length, and the screws then tightened to fix that length. To accomplish this, the set screws 68, when tightened, can provide a friction fit with the inner telescoping strut member or can engage in a selected hole of a row of longitudinally spaced holes (not shown) in that inner strut member.

Figure 9:
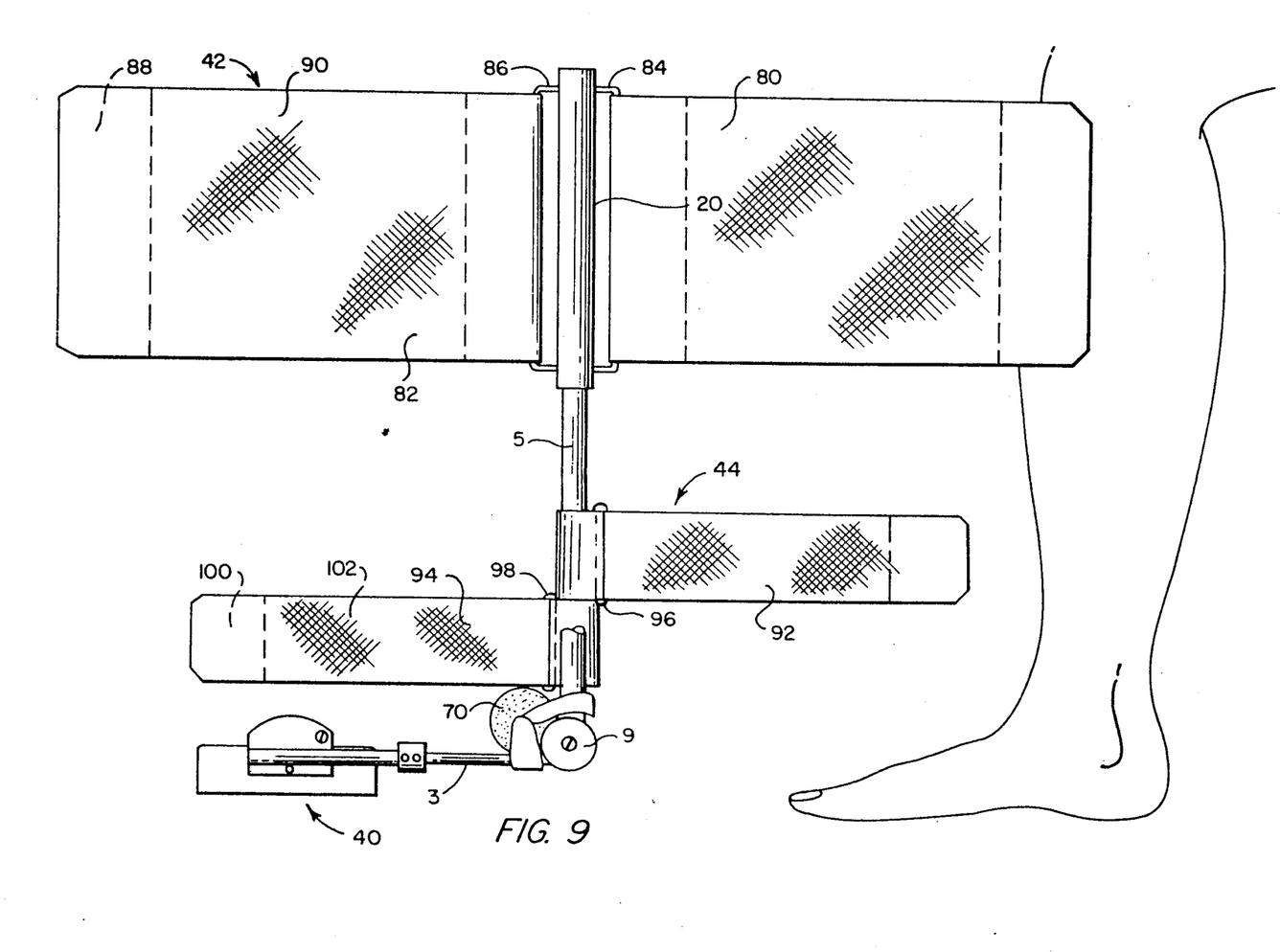
FIG. 9 is a side elevational view of the splint device of the invention, as spread out prior to the application thereof to a patient, showing details of the supporting cuffs and straps.

Although any suitable arrangement can, in general, be used to secure pivotally mounted struts 3, 5 and 3a, 5a to the limb of a patient, a preferred embodiment of such an arrangement will now be described. It will be appreciated that a suitable arrangement must provide that the struts are positioned laterally of the ankle joint, with the axes of rotation at pivot heads 9, 9a coinciding closely as possible with the axis of rotation of the ankle joint. The preferred arrangement referred to above comprises the upper cuff assembly 42, and lower strap assembly 44 which were mentioned above and which are best seen in FIGS. 4 and 9. As shown, upper cuff assembly 42 includes a calf cuff 80 and shin cuff 82 both of which are, as shown in FIG. 9, secured at the end thereof to the upper ends of strut 5 adjacent to biasing mechanism 20. Further , although this is not illustrated in FIG. 9, it will be understood that calf cuff 80 and shin cuff 82 are affixed at the opposite ends thereof to strut 5a adjacent the associated mechanism 20. In particular, oppositely extending inverted U-shaped (see also FIG. 1) supports 84 and 86 that are integrally formed by a generally rectangular loop member welded or otherwise affixed to struts 5 and 5a define a pair of openings through which the opposite ends of calf cuff 80 and shin cuff 82 extend. It will be understood that calf cuff 80 and shin cuff 82, respectively, extend between the pairs of supports 84 and 86 formed on upper struts 5 and 5a (See FIG. 1) and can be attached to the corresponding supports in a number of different ways so long as, in accordance with a preferred embodiment, some adjustment thereof is permitted. For example, a combination hooks and loops fastener can be provided at both ends of the cuffs 80, 82 so as to enable these ends to be inserted through the openings defined by supports 84 and 86 and then folded back to engage the hooks and loops together, thereby securing the cuffs in place.

Figure 8:
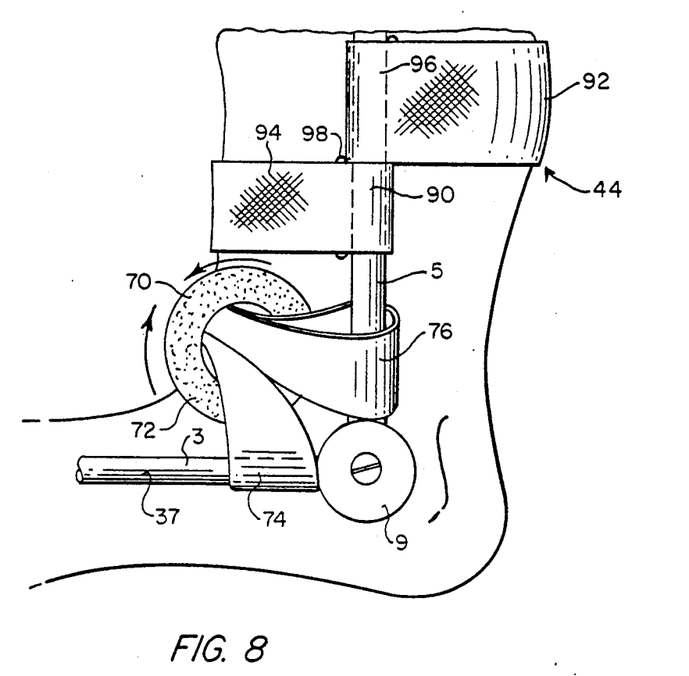
FIG. 8 is a side elevational view, drawn to an enlarged scale and partially broken away, of the splint device of FIG. 4 in place on a patient.

In the specific embodiment shown in FIGS. 8 and 9, one end of calf cuff 80 is secured to support 84, and one end of shin cuff 82 is secured to support 86, by folding over the free cuff ends and sewing these free ends to the body of the cuff, thereby forming a loop in which the corresponding support is received. In this embodiment, supports 84 and 86 are advantageously of the form shown in FIG. 10 wherein the supports 84, 86 are discontinuous, i.e., include a gap or opening in the middle thereof, between the free ends of the two halves of the supports so as to permit the corresponding cuff loop to be inserted therein. This enables the cuffs to be removed for cleaning, replacement and the like. It will be appreciated that in this exemplary embodiment the opposite ends of each half of the supports 84, 86 are welded to the respective upper strut 5 or 5a. Further, as illustrated for support 84, an internally threaded telescoping element 84 can be provided which enables the gap or opening between the halves to be closed off by screwing element 84 onto the upper half of support 86, thereby also strengthening the support.

In the embodiment of FIG. 9, the other ends of the cuffs 80 and 82 are provided with hook and loop fasteners, as indicated by the section of hooks, denoted 88, and the spaced section of loops, denoted 90, for shin cuff 82. Thus, by inserting the free end of shin cuff 82 through the opening defined by the support 86 on the opposing upper strut 5a, and then bringing the hooks and loops together, the shin cuff 82 can be properly positioned and tightened in place around the shin of a wearer. It will be understood that the hook and loop fastener sections 88 and 90 are one example of a suitable arrangement for permitting adjustment, i.e., tightening, of cuff 82 around the shin of a patient and that other arrangements can be used. It will also be appreciated that calf cuff 80 is fitted and tightened around the calf of a patient or other wearer in a similar manner.

Shin and calf strap assembly 44 is similar to shin and calf cuff assembly 42 and comprises a calf strap 92 and a shin strap 94. In the embodiment illustrated in FIGS. 8 and 9, belt-type loops 96 and 98 are sewed or otherwise affixed to one end of straps 92 and 94, respectively, and the other ends of the straps inserted through loops 96 and 98 so that the straps 92 and 94 encircle or are wrapped around strut 5 so as to fix the loop ends in place on strut 5. The other ends of straps 92 and 94 are simply wrapped around the opposing strut 5a and held in place by hooks and loop fasteners, as indicated by hooks section 100 and loops section 102 of shin strap 94.

The arrangement for securing of the adjustable ankle splint to the limb of patient also includes an adjustable ankle strap assembly 70 (best seen in FIGS. 4 and 8) which is attached to the upper and lower strut members about the ankle joint on each side of the strut assembly. The ankle assembly 70 comprises an outer tube 72 of a soft material such as soft rubber and a pair of strap fasteners 74 and 76 which extend through the outer tube 72. The strap fasteners include hook and loop fasteners (not shown) at both ends thereof which enable these ends to close on themselves after being looped around the respective struts 3, 3a and 5, 5a as is indicated for struts 3 and 5 of FIG. 8.

Figures 10, 13:
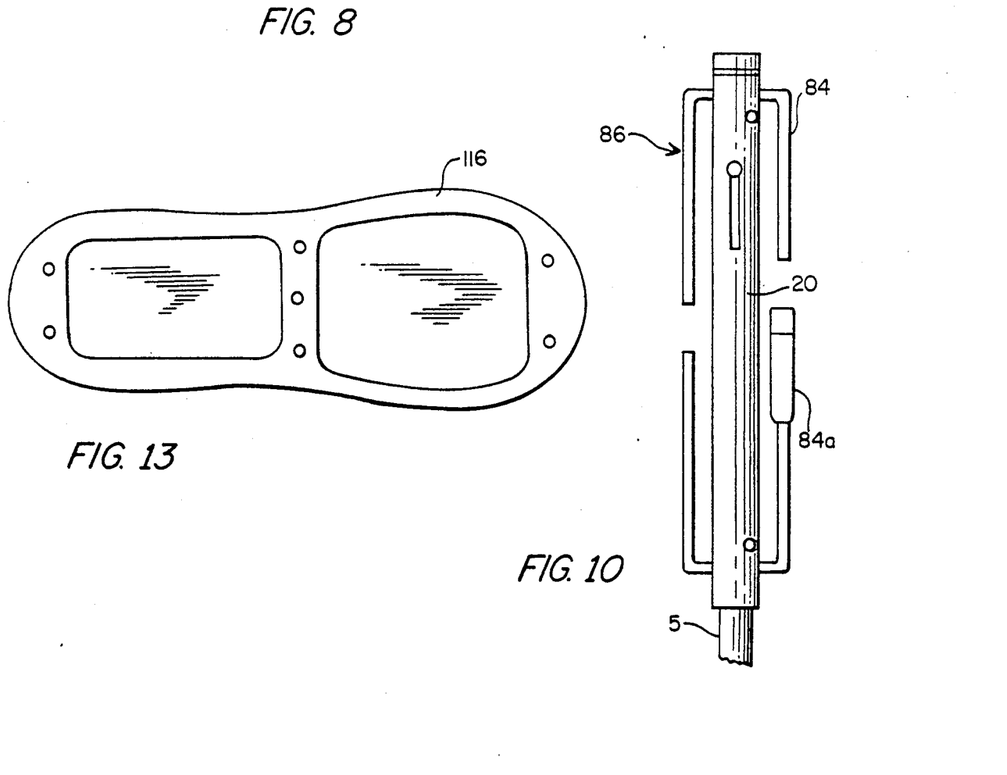
FIG. 10 is a side elevational view, partially broken away, of an tension adjustment mechanism for the splint device, showing a further embodiment of a cuff support arrangement.
FIG. 13 is a top plan view of a elevation adjustment member used with the elevating shoe of FIGS. 11 and 12.
Figure 11:
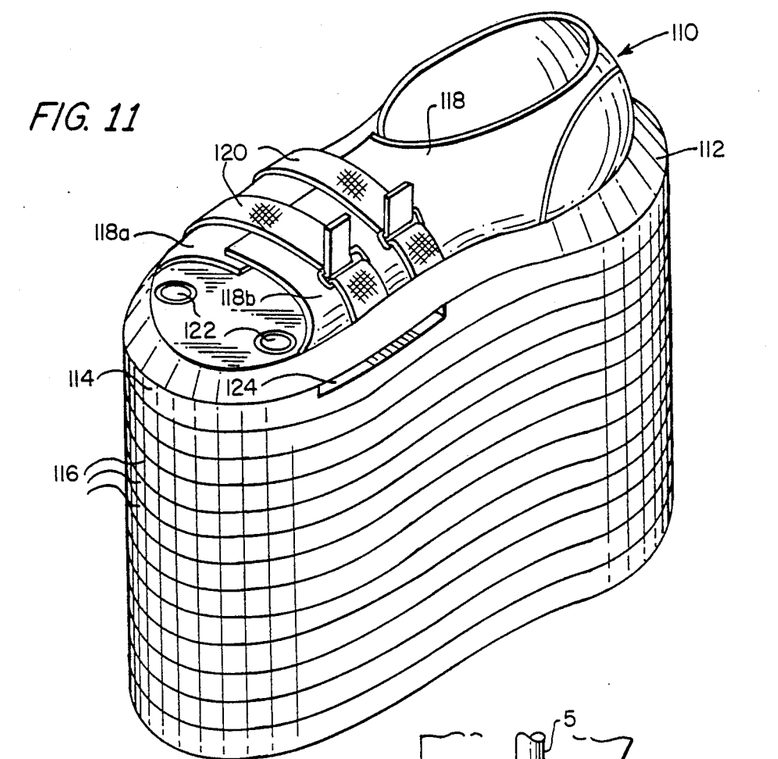
FIG. 11 is a perspective view of a elevating shoe adapted to be used with the splint device of the invention in accordance with a further embodiment thereof.
Figure 12:
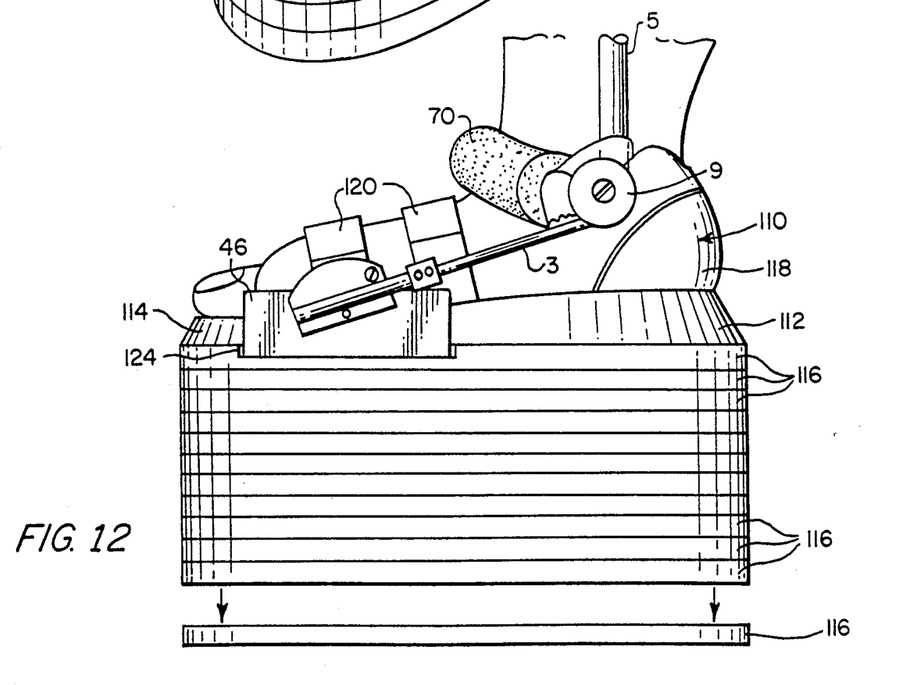
FIG. 12 is a side elevational view of the elevating shoe of FIG. 11 in combination with the splint device of FIG. 4.

Referring to FIGS. 11 to 13, a further aspect of the invention is illustrated. FIG. 11 shows a shoe 110 having a relatively soft sole portion 112 mounted on an upper plate member or plate 114, fabricated of plastic or the like, which supports a plurality of further, shaped plates 116, shown in more detail in FIG. 13 and disposed in stacked relation. Shoe 110 includes an upper portion 118 which is constructed in the same general manner of an open-toed running shoe and separable front parts or portions of which, denoted 118a and 118b, are connected together by straps 120 including hooks and loops fasteners (not shown) so as to permit these portions 118a, 118b to be opened, to thus allow the foot of a wearer to be placed into the shoe, and then closed around the foot in a conventional manner. Shoe 110 is affixed to upper plate member 114 by suitable means such as screws or bolts, two of which are indicated at 122.

Upper plate member 114 includes a slot or opening 124 extending therethrough into which the footplates 46 and 48 of footplate assembly 40 are inserted. The size of slot 124 is chosen such that the footplate 46, 48 form a tight fit therewith and any screw connections between plates 46, 48 can be eliminated since lateral adjustment is not required in any event. This is illustrated in FIG. 12 which shows the foot of a patient received in shoe 110 and the splint assembly discussed above in place, with plate 46 received in the slot 124 in upper plate member 114. It will be appreciated that the provision of shoe device shown in FIGS. 11 to 13 results in more comfortable support for the foot and in general tends to spread out the forces exerted over a broader area of contact.

An important feature of the stacked plate assembly formed by plates 116 is that it permits plates 116 to be added to and removed from the stack, as desired, so as to vary the height of the stack and thereby accommodate the lengthening of the limb of a patient as treatment progresses. To explain, the limb of a patient may be temporarily shortened by, for example, a disease or a trauma suffered during an accident but may be caused or permitted to lengthen as treatment proceeds. Thus, a relatively high stack of plates 116 may be required initially so that the two limbs of the patient are of the same length. However, as treatment progresses, and the limb lengthens, the number of plates 116 can be reduced to accommodate this. Plates 116 can be removed readily by simply removing screws or rivets (not shown) provided in the screw holes or openings 126 (see FIG. 13).

The adjustable spring-loaded mechanism of the splint device of the present invention allows for adjustment of quantifiable force on an extremity acting across the body joint from 0 foot poundage up to the maximum desired foot poundage, at various body joint ranges as needed. For example, in a patient having an ankle flexion contracture of 30°, the splint device can be applied to the ankle with built-in tension of 5 foot pounds of force acting on the calf at a 30° ankle flexion angle. As the patient develops greater tolerance to the device in the days that follow, greater force can be adjusted in the mechanism by simply adjusting the tension (e.g. using the "Allen" wrench indicated at 32 in FIG. 4) and causing greater compression of the spring in the corresponding strut. This will provide a greater compression of the spring in the strut which will therefore exert a greater force tending to extend the joint. On the other hand, if the patient has a flexion contracture of 45°, the same tension could be dialed into the splint at the angle just as could be done at 30°, and just as could be done at a 10° ankle flexion contracture. In other words, any force up to maximum capability of the spring employed in the strut can be dialed at any angle of ankle flexion. In addition, the invention permits the interchangability of springs of different force-exerting capabilities so as to allow for varying the degrees of tension exerted by the spring mechanism depending upon the particular use to which the device is applied.

One example of a particular case in which the adjustable splint of the invention can be used for flexion of a joint is in connection with an extension contracture, i.e., a loss of ability to flex the ankle joint through the normal range of motion. In an ankle extension contracture, whether the contracture is of a muscle or joint type, the individual may be able to flex the ankle to 25° and no further. The force exerted by the splint device can be adjustable from 0 foot pounds of torque across the ankle joint to upward torque of whatever tension capability the particular spring being used would have. The exact tension desired would be determined by factors such as patient tolerance, type and age of the contracture, skin compliance, diagnosis, etc.

An important feature of the splint device of the invention as applied to the ankle is the ability of the device to allow graduated, quantified, adjustable tension, combined with the attendant ability to relax the stretch across the joint by extending the ankle away from the limit of flexion. This will allow the tissue being stretched to have a rest period while not disturbing the adjustment of the spring tension and without having to remove the splint. In order to relieve the pressure of the contractured tissues, one merely has to overcome, by any means, the tension in the splint and extend the joint to a comfortable posture. Once a short rest is achieved, the splint may again exert its tension against the contractured tissue to help accomplish a greater degree of flexion in the joint. The time necessary to accomplish the optimal result using the splint device of the invention would vary depending on many factors, some of which have been mentioned above and include are the patient's diagnosis, age of patient, age of the contracture and tolerance of the patient.

While the invention has been disclosed with reference to specific exemplary embodiments, it will be understood that variations and modifications can be effected in these embodiments without departing from the scope of the invention.

What is claimed is:

1. An adjustable splint device for supporting the ankle of a wearer, said splint device comprising:
   (a) a pair of strut assemblies adapted to be positioned on opposite sides of the ankle of a wearer, each of said strut assemblies comprising an upper strut, and a lower strut pivotably connected to said upper strut, one of the struts of at least one of said strut assemblies including at one end thereof a pivotably mounted heat portion defining a cam surface, and the strut connected to said one strut including an adjustable biasing means, mounted therein and biased into engagement with said cam surface, for applying a quantifiable force tending to align or approximate said upper and lower struts;
   (b) foot support means, connected to said pair of strut assemblies, for supporting the foot of a wearer; said foot support means comprising a foot support device; pivot means for pivotably connecting said foot support device to the lower struts of said strut assemblies; and adjustable locking means for selectively fixing the angular position of said foot support device relative to said lower struts so that the foot of a wearer is held in a predetermined position relative to the ankle of the wearer; and
   (c) securing means for releasably securing said strut assemblies to the lower leg of the wearer.

2. An adjustable splint device as claimed in claim 1 wherein said foot support device comprises a pair of laterally adjustable footplates.

3. An adjustable splint device according to claim 2 wherein each said footplate includes an upwardly projecting portion at the outermost edge thereof having an arcuate slot therein, wherein said pivot means comprises a connection plate disposed at the distal end of, and pivotably connected to, a respective said projecting portion, and wherein said locking means comprises an adjustable fastening means extending through said arcuate slot for fixing the position of said connection plate relative to said projecting portion.

4. An adjustable splint device according to claim 2, further comprising width setting means for adjustably setting the lateral positions of the foot support plates so as to accommodate different foot widths.

5. An adjustable splint device according to claim 4, wherein said width adjustment means includes at least one adjustment screw located on an underside area of the foot support plates for engaging said foot support plates to thereby set a predetermined width.

6. An adjustable splint device according to claim 1, further comprising adjustable length setting means for adjustably setting the axial position of said foot support means so as to selectively shorten or lengthen the splint device.

7. An adjustable splint device according to claim 6, wherein said each lower strut includes a pair of telescoping sections and said length adjusting means includes at least one set screw for fixing the relative positions of said telescoping sections so as to set the combined length of the sections.

8. An adjustable splint device according to claim 1, wherein said securing means comprises adjustable instep strap means, connected to at least one pair of said struts, for engaging the front of the ankle joint of the wearer.

9. An adjustable splint device according to claim 8, wherein said instep strap means comprises a resilient tube and a fastening means, which includes at least one hooks and loops fastener and which is of adjustable length and extends through said tube, for fastening said tube to said splint assemblies.

10. An adjustable splint device according to claim 1, wherein said securing means comprises strap means, attached to and extending between at least one pair of struts of each said strut assembly, for securing the splint assemblies to the limb of a wearer above the ankle joint.

11. An adjustable splint device according to claim 10, wherein said strap means comprises:
   (a) a first lower strap of a length sufficient to wrap across the shin area of the limb of a wearer and means for adjustably and releasably fastening said first strap between the strut assemblies;

(b) a second lower strap of a length sufficient to wrap across a lower rear area of the limb of a wearer and means for adjustably and releasably fastening said second strap between the strut assemblies;

(c) a first upper cuff of a length sufficient to wrap across an upper shin area of the wearer and means for adjustably and releasably securing said first cuff between the strut assemblies; and (d) a second upper cuff having a length sufficient to wrap across a calf area of the wearer and means for adjustably and releasably securing said second cuff between the strut assemblies.

12. An adjustable splint device according to claim 11, the first and second upper cuffs are of the same width, and the first and second lower straps are of the same width and are more narrow in width than said upper cuffs.

13. An adjustable splint as in claim 11, wherein said first and second upper cuffs each comprise, at least one end thereof, fastening means comprising a loops fastener section spaced apart from a hooks fastener section.

14. An adjustable splint as in claim 1, wherein said foot support device includes a shoe device in which the foot of the wearer can be received.

15. An adjustable splint as in claim 14, wherein said shoe device includes a sole of variable height.

16. An adjustable splint as in claim 15, wherein said sole comprises a plurality of stacked, removably mounted sole members which can be removed to change the height of the sole.

17. An adjustable splint as in claim 14, wherein said shoe device includes a sole having an upper slot therein and wherein said foot support device further includes a pair of laterally adjustably overlapping plates which are received in said slot and which connect said shoe to said strut assembly.

* * * * *